United States Patent [19] [11] Patent Number: 4,556,057
Hiruma et al. [45] Date of Patent: Dec. 3, 1985

[54] CANCER DIAGNOSIS DEVICE UTILIZING LASER BEAM PULSES

[75] Inventors: Teruo Hiruma; Atsushi Honma; Tooru Hirano; Yutaka Tsuchiya, all of Hamamatsu; Yoshihiro Hayata, Tokyo; Katsuo Aizawa, Tokyo; Harubumi Kato, Tokyo; Keiji Kainuma, Tokyo, all of Japan

[73] Assignee: Hamamatsu TV Co., Ltd., Hamamatsu, Japan

[21] Appl. No.: 474,302

[22] Filed: Mar. 11, 1983

[30] Foreign Application Priority Data

Aug. 31, 1982 [JP] Japan .................... 57-151404

[51] Int. Cl.[4] .............................................. A61B 6/08
[52] U.S. Cl. ................................. 128/303.1; 128/395; 128/634; 128/654; 604/20
[58] Field of Search ............ 128/303.1, 395, 665–667, 128/654, 634, 633, 632; 219/121 LM, 121 LE, 121 LF; 250/327.1, 458, 458.1; 351/13; 364/414; 356/138; 358/93; 604/20, 53

[56] References Cited

U.S. PATENT DOCUMENTS

| 4,178,917 | 12/1979 | Shapiro | 128/633 |
| 4,184,175 | 1/1980 | Mullane, Jr. | 250/562 |
| 4,195,641 | 4/1980 | Joines et al. | 128/632 |
| 4,213,462 | 7/1980 | Sato | 128/634 |
| 4,222,389 | 9/1980 | Rubens | 128/633 |
| 4,266,549 | 5/1981 | Kimura | 128/654 |
| 4,302,672 | 11/1981 | Kato et al. | 250/337 |
| 4,310,886 | 1/1982 | Kato et al. | 250/363 R |
| 4,313,057 | 1/1982 | Geibwachs | 356/311 |
| 4,350,163 | 9/1982 | Ford, Jr. et al. | 128/633 |
| 4,355,871 | 10/1982 | Nevyas et al. | 356/376 |
| 4,396,285 | 8/1983 | Presta et al. | 128/303.1 |
| 4,449,535 | 5/1984 | Renault | 128/634 |
| 4,512,762 | 4/1985 | Spears | 604/53 |

FOREIGN PATENT DOCUMENTS

| 159142 | 10/1981 | Japan . | |
| 1045868 | 10/1966 | United Kingdom . | |
| 1073619 | 6/1967 | United Kingdom . | |
| 1135956 | 12/1968 | United Kingdom . | |
| 1320170 | 6/1973 | United Kingdom . | |
| 1378986 | 1/1975 | United Kingdom . | |
| 2023004 | 12/1979 | United Kingdom . | |
| 1573748 | 8/1980 | United Kingdom . | |
| 2074343 | 10/1981 | United Kingdom . | |
| 2075668 | 11/1981 | United Kingdom . | |
| 2076993 | 12/1981 | United Kingdom . | |
| 0055032 | 9/1982 | United Kingdom | 128/634 |

Primary Examiner—C. Fred Rosenbaum
Assistant Examiner—Gene B. Kartchner
Attorney, Agent, or Firm—Spencer & Frank

[57] ABSTRACT

Cancer diagnosis device contains an endoscope comprising a light pipe used to transmit light beams from respective light sources and an image guide used to observe the flesh of the organism during both diagnosis and treatment. The tip of the endoscope faces toward the focuses where a photosensitive material having an affinity to the focuses of cancer has been absorbed so that a treatment for cancer can be performed by exposing the organism affected by cancer to the laser beam. The attainable the laser beam within a focus is thus increased by the use of the laser beam pulse from a first laser beam pulse source. In addition to the above, the cancer diagnosis device contains a second laser beam pulse source used to transmit a light beam to the focuses through the light pipe for making a diagnosis, a selector used to selectively pick up the light beam from the first laser beam pulse source or the second laser beam pulse source, a spectroscope used to obtain the spectral response from emission of light led through the image guide used for observation from the flesh of the organism where fluorescence occurs, an imaging device used to pick up the spectral response, a graphic display used to graphically display the processed spectra picked up by the imaging device, and a controller used to control emission of light from the second laser beam pulse source and also to make the operation of the imaging device synchronize with the second laser beam pulse source.

7 Claims, 11 Drawing Figures

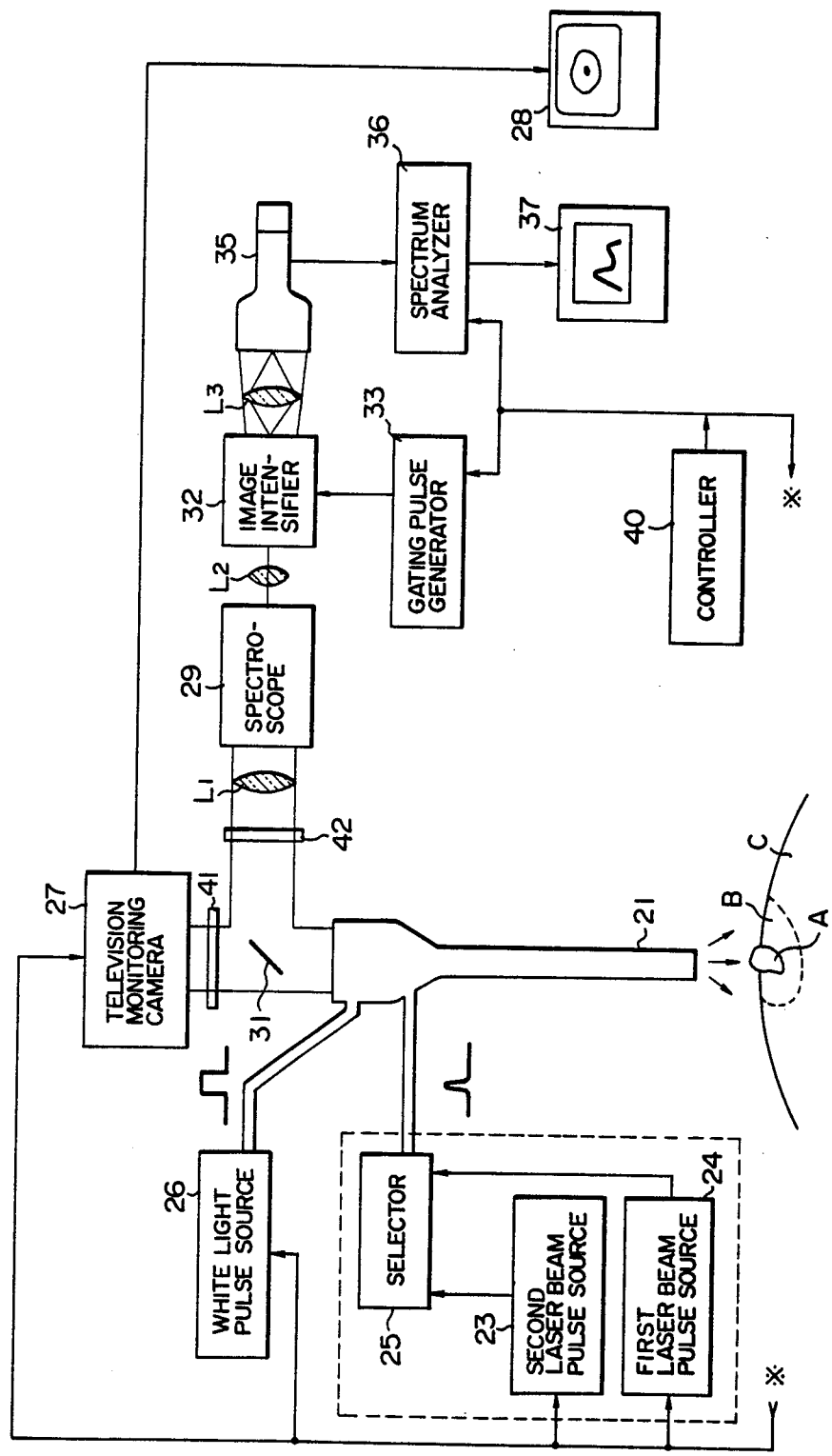

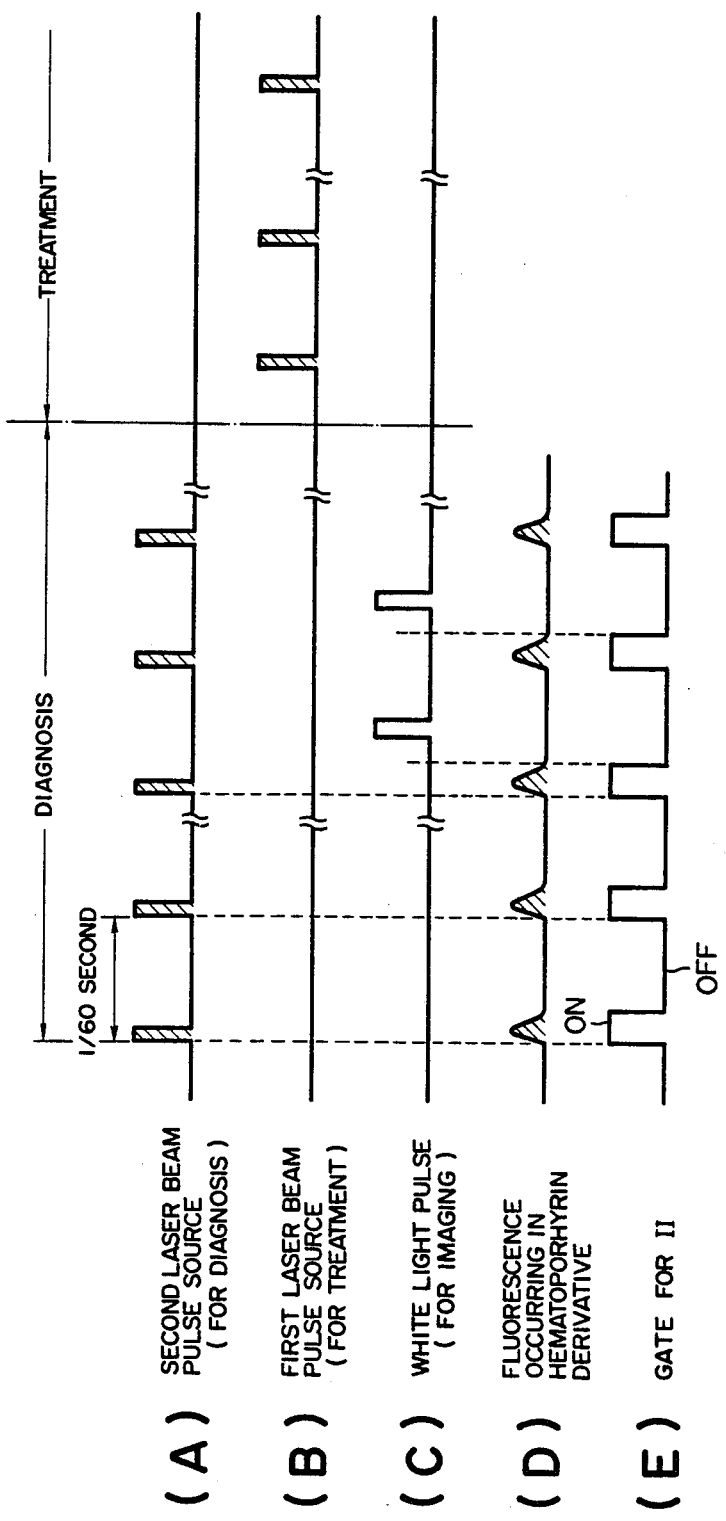

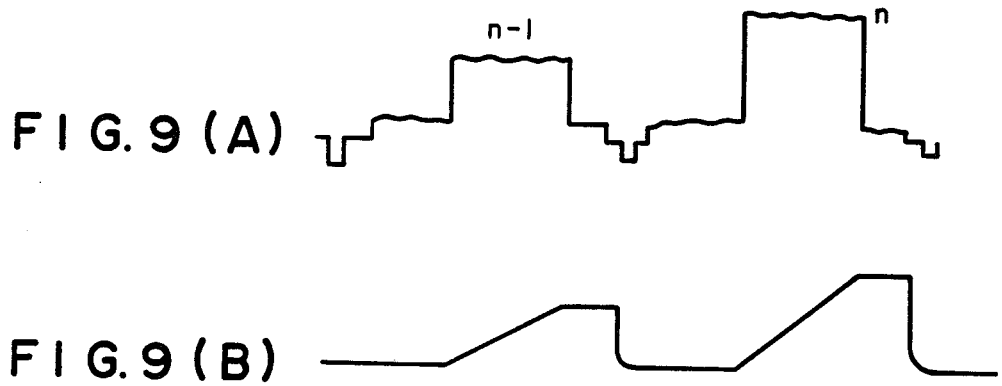
FIG. 9(A)
FIG. 9(B)
FIG. 10
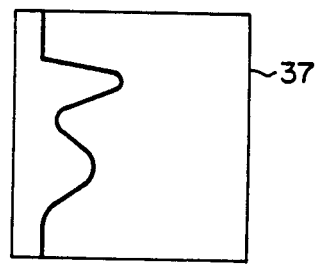

CANCER DIAGNOSIS DEVICE UTILIZING LASER BEAM PULSES

BACKGROUND OF THE INVENTION

This invention relates to a device used to diagnose the focuses of cancer, and particularly to a device for irradiating a cancer with a laser beam where a photosensitive material such as hematoporphyrin derivatives having an affinity to cancer and other tumors has beforehand been absorbed by the cancer.

Continuous krypron laser beams have been used for a diagnosis of cancer, and continuous argon laser beams have been used for a treatment of the focuses of cancer. Devices used for these purposes have been proposed (Japanese Utility Model Application No. 159142/1981 filed by Yoshihiro Hayata, Katsuo Aizawa and Harubumi Kato).

FIG. 1 shows the schematic diagram of the device according to the above-mentioned Japanese Utility Model application. In the device shown, hematoporphyrin derivative is beforehand absorbed in both focus A of the cancer and its peripheries B before the start of a diagnosis of the cancer. Endoscope 1 faces the focus A and its peripheries B.

Visible rays from krypton laser beam source 5 are selectively transmitted through mirror 7 to light pipe 12, and they are incident upon focus A and its peripheries B. An image of focus A and its peripheries B is picked up by use of image guide 11, and then it is fed to image intensifier 3 through bandpass (color) filter 2 in order to observe the image.

For the treatment of the affected part of flesh, visible rays from argon dye laser source 6 are transmitted through light pipe 12 thereto.

This device permits the diagnosis and treatment to be carried out in a new mode. However, it is difficult for the focuses of cancer in the early phase to be detected. The reason is as described below.

When a hematoporphyrin derivative has been absorbed in focus A of cancer and its peripheries B, fluorescence occurs in these locations peaking at both 630 nm and 690 nm. The magnitude of fluorescence for the focuses of cancer in the early phase is much lower than that in the intermediate phase, and its spectral response is obscure. Fluorescence occurring in focus A of cancer and its peripheries B is magnified by image intensifier 3 shown in FIG. 1. Therefore, fluorescence peaked at both 630 nm and 690 nm from a hematoporphyrin derivative cannot easily be distinguished from that at 570 through 580 nm from the flesh not affected by cancer. Thus, cancer in the early phase cannot easily be detected.

In order to solve the aforementioned problem, the inventors of the present invention found that imaging of the spectral response should be synchronized with irradiation of the laser beam pulse used for a diagnosis so as to distinguish, as far as possible, fluorescence occurring from the flesh not affected by cancer from that occurring from the focuses of cancer. The inventors found that data for use in a precise diagnosis could be obtained by analyzing the image picked up by the aforementioned method.

The objective of the present invention is to present a cancer diagnosis device utilizing a laser beam pulse to facilitate detection of cancer in the early phase.

The other objective of the present invention is to present a cancer diagnosis device providing the capability to perform a spectrum analysis and also to observe the focuses of cancer without any interference to the spectrum analysis.

SUMMARY OF THE INVENTION

The cancer diagnosis device in accordance with the present invention contains an endoscope comprising a light pipe used to transmit light beams from respective light sources and an image guide used to observe the flesh of the organism during both diagnosis and treatment. The tip of the endoscope is positioned to face the focuses where a photosensitive material having an affinity to the focuses of cancer has been absorbed so that a treatment for cancer can be performed by exposing the organism affected by cancer to the laser beam. The attainable depth of the laser beam within a focus is thus increased by the use of a laser beam pulse from a first laser beam pulse source. In addition to the above, the cancer diagnosing device contains a second laser beam pulse source used to transmit a light beam to said focuses through said light pipe for making a diagnosis, a selector used to selectively pick up the light beam from said first laser beam pulse source or said second laser beam pulse source, a spectroscope used to obtain the spectral response from emission of light led through the image guide used for observation from the flesh of the organism where fluorescence occurs, an imaging device used to pick up said spectral response, a graphic display used to graphically display the processed spectra picked up by said imaging device, and a controller used to control emission of light from said second laser beam pulse source and also to make the operation of said imaging device synchronize with said second laser beam pulse source.

BRIEF DESCRIPTION OF THE DRAWINGS

FIG. 2 is a block diagram of a preferred embodiment of the cancer diagnosis device in accordance with the present invention;

FIG. 4 depicts a timing chart showing the operation of the cancer diagnosis device in accordance with the present invention;

FIG. 9 shows the waveforms of the video signals and the video signals after integration, and;

FIG. 10 is a view showing an example of the spectral response.

DESCRIPTION OF THE PREFERRED EMBODIMENT

Figure 1:
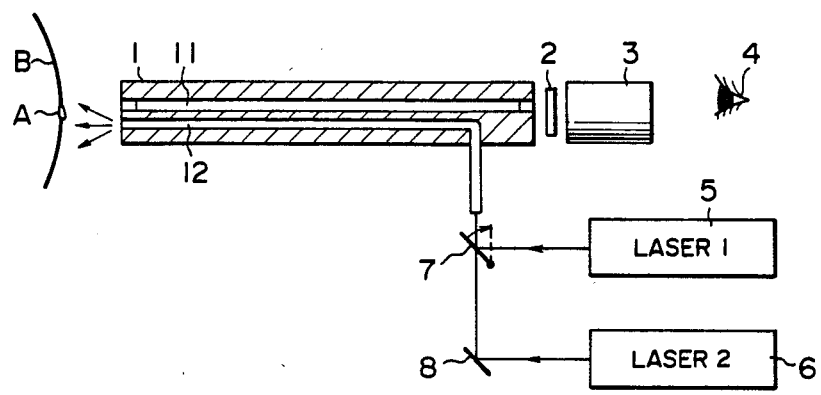
FIG. 1 shows a schematic diagram of the conventional cancer diagnosis and treatment device.

Referring to the drawings, the present invention will be described hereinafter in detail.

In FIG. 2, marks A, B and C represent a focus of cancer, its peripheries and the flesh of an organism not affected by cancer, respectively.

A hematoporphyrin derivative with a pH of 7.4 formed by dissolving hematoporphyrin hydrochloride having an affinity to the focuses of cancer in a mixture of sulfuric acid and acetic acid is used as a solution for intravenous injection. Prior to the diagnosis the above-mentioned hematoporphyrin derivative is to be injected into the vein of a patient.

A hematoporphyrin derivative is a harmless material selectively absorbed in the organism affected by cancer but not in the organism which is not affected by cancer. When the second laser beam pulse with a wavelength of approximately 405 nm from the second laser beam pulse source is incident upon a hematoporphyrin derivative absorbed into the focuses of cancer, fluorescence occurs at both wavelengths of 630 nm and 690 nm.

Figure 3:
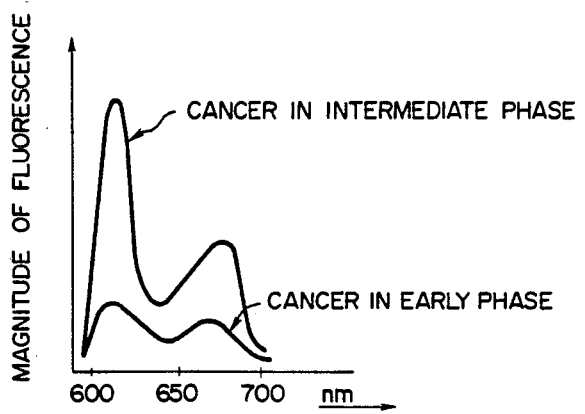
FIG. 3 is a graph showing fluorescence occurring in a hematoporphyrin derivative absorbed in the focuses of cancer.

As described in relation to FIG. 3, fluorescence of a hematoporphyrin derivative absorbed in the focuses of cancer in the early phase is weak because the absorbed hematoporphyrin derivative is small in quantity. In this condition, fluorescence can occur in the flesh of the organism not affected by cancer. These cannot be distinguished by the conventional technique.

The cancer diagnosis device in accordance with the present invention, however, analyzes fluorescence so as to precisely diagnose the focuses of cancer in such a manner as described below.

Endoscope 21 contains a light pipe to transmit the light pulse to be incident upon the focuses of cancer and its peripheries.

The preferred embodiment of the cancer diagnosis device consists of a first laser beam pulse source 24 used for treatment, a second laser beam pulse source 23 for a precise diagnosis, and a white light pulse source 26 used as the third light pulse source for the overall diagnosis.

Visible light from first or second laser beam pulse source 24 and 23 is selectively applied to a light pipe and that from white light pulse source 26 is applied to another light pipe. Visible light is then fed to the focuses of cancer.

Figure 5:
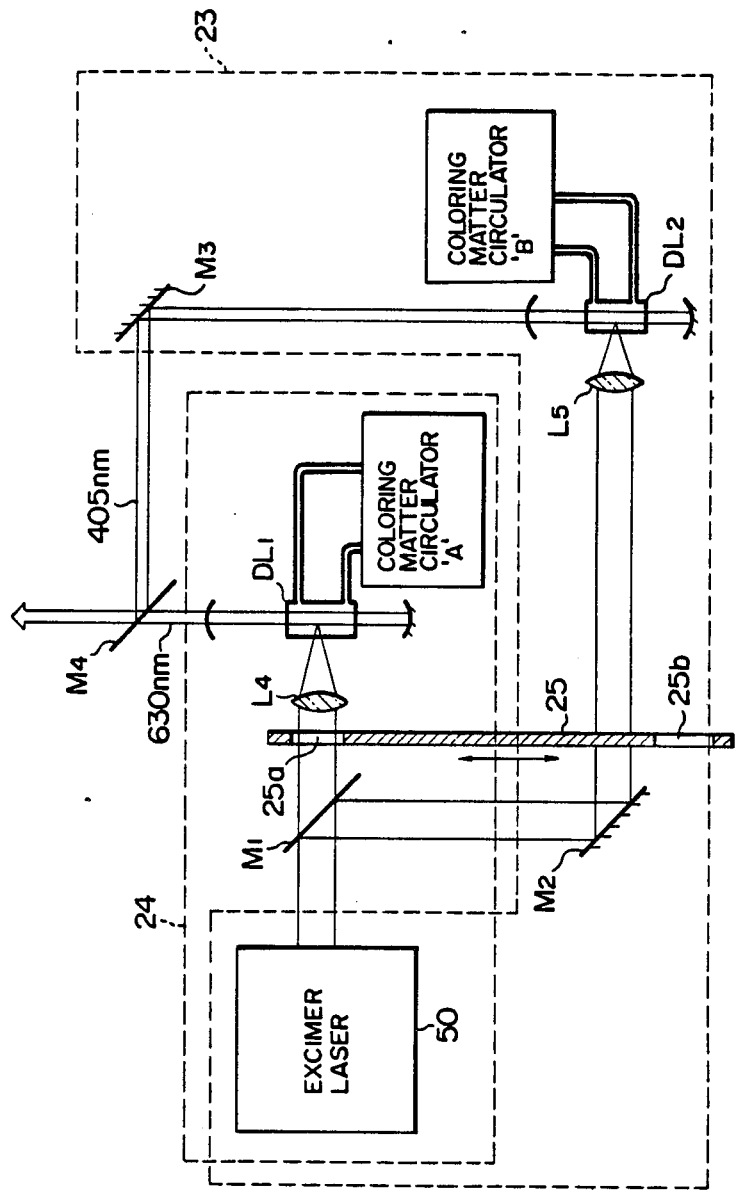
FIG. 5 is a block diagram showing the structure of the laser beam pulse sources.

FIG. 5 shows an example of first and second laser beam pulse sources 24 and 23. In FIG. 5, the first laser beam pulse source emitting visible light at 630 nm is enclosed within a broken line 24 and the second laser beam pulse source emitting visible light at 405 nm is enclosed within a broken line 23.

Excimer laser 50 is commonly used for first and second laser beam pulse sources 24 and 23. First color laser DL1 can emit visible light at 630 nm when stimulated by excimer laser 50. Second color laser DL2 can emit visible light at 405 nm when stimulated by excimer laser 50. L4 and L5 are condenser lenses, respectively. M1 and M4 are semi-transparent mirrors, respectively. M2 and M3 are total reflection mirrors, respectively. Selector 25 is a shutter with two openings 25a and 25b, and can be manually operated. Color laser DL1 is stimulated by the laser beam fed from excimer laser 50 through a light path formed by opening 25a and lens L4 during treatment. Color laser DL2 is stimulated by the laser beam fed from excimer laser 50 through a light path formed by opening 25b and lens L5.

Excimer laser 50 can emit light pulses with energy ranging from several milli-joules to 100 milli-joules with a pulse width of 30 ns at a wavelength of 308 nm at a repetition rate of 60 Hz or a fraction of 60 Hz.

It is difficult for the light beam at a wavelength of 630 nm selected as the first laser beam pulse to be absorbed into a living organism. The light beam at 630 nm, however, can efficiently be absorbed into hematoporphyrin derivatives.

Fluorescence as shown in FIG. 3 can occur in the focus of cancer when light at a wavelength of 405 nm fed from the second laser beam pulse source 23 impinges on a cancer.

Visible light from white light pulse source 26 in FIG. 2 is led to the second light pipe of the endoscope for observation. Images of portions A and B can be observed under illumination by the white light pulse source 26, and these are displayed on a television picture monitor to be described hereinafter.

The entire system of the cancer diagnosis device in accordance with the present invention is controlled by controller 40 which can generate a basic timing signal clocked at 60 Hz so that excitation of the laser beam pulse sources, reproduction of images, and spectrum analysis can synchronously be performed. The basic timing signal will be described later when the operation of the entire device will be explained.

Figure 6:
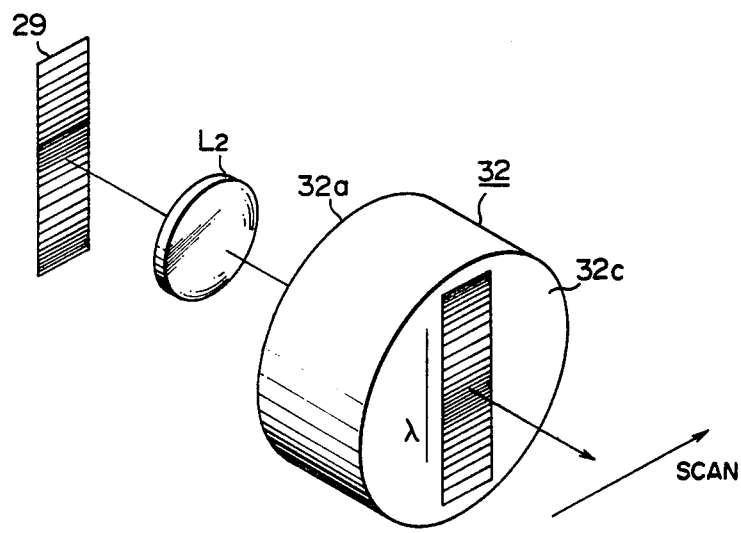
FIG. 6 is a perspective view of an image on the photoelectric layer of the image intensifier when the spectral response is obtained by a spectroscope.

Semi-transparent mirror 31 faces the outlet of the image guide in endoscope 21. An image led from the image guide goes through semi-transparent mirror 31 into two directions. An image passing through semi-transparent mirror 31 is applied to television camera 27 through shutter 41 which can open only during diagnosis. An image of portion A or B obtained by the laser beam from second laser beam pulse source 23, the light pulse from white light pulse source 26, or by both of these pulses can be picked up by television monitoring camera 27 during diagnosis, and then it can be displayed on television picture monitor 28. An image reflected from semi-transparent mirror 31 is applied to spectroscope 29 through shutter 42 and condenser lens L1. Spectroscope 29 is used to analyze an image of portion A or B. An image from spectroscope 29 is incident upon photoelectric layer 32a of image intensifier 32 through condenser lens L2. FIG. 6 depicts a schematic diagram showing how the image from spectroscope 29 is incident upon the photoelectric layer of image intensifier 32.

Figure 7:
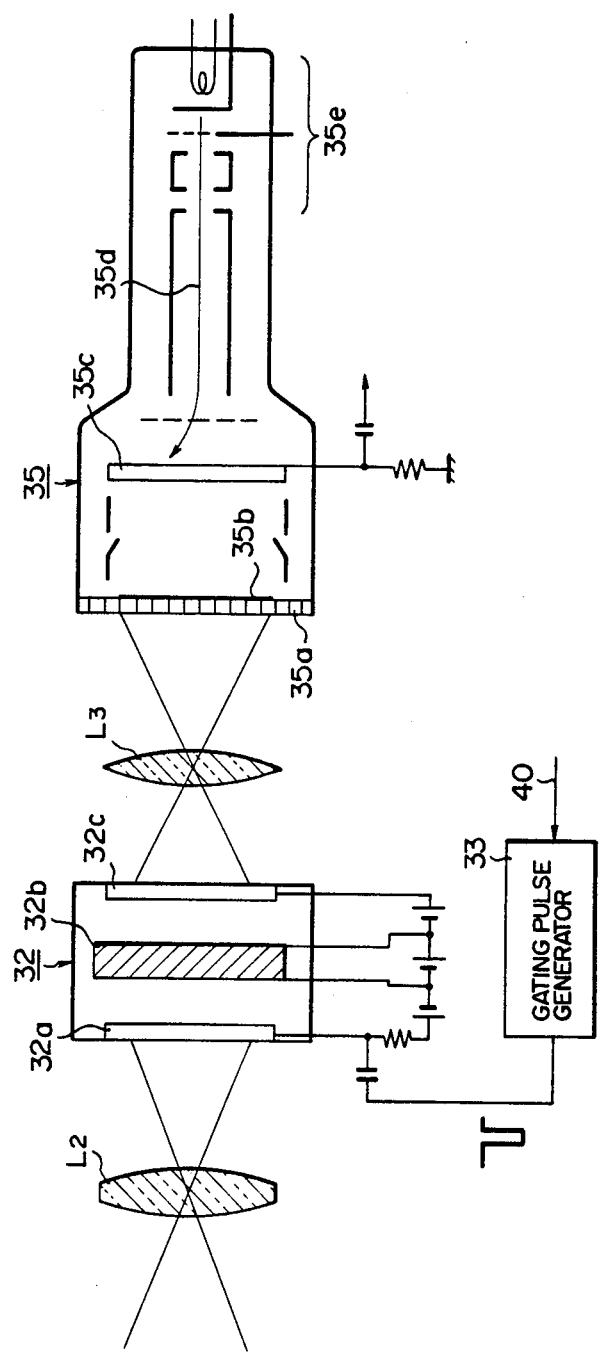
FIG. 7 is a schematic diagram showing the image intensifier and imaging tube.

Image intensifier 32 is used to send the spectra of the image for the focuses of cancer from photoelectric layer 32a to phosphor layer 32c through microchannel plate 32b which is clearly shown in FIG. 7.

FIG. 7 shows the locational relation between image intensifier 32 and SIT imaging tube 35.

Figure 8:
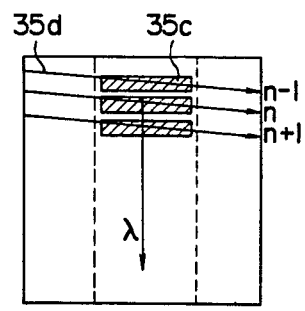
FIG. 8 depicts a schematic diagram showing the relation of the spectral response to the scanning lines in the television monitoring system.

The imaging tube 35 consisting of faceplate 35a, photoelectric layer 35b formed on the inner plane of faceplate 35a, image target 35c, and electron gun 35e is used to generate a graphical signal of the spectral response. An image formed on image target 35c corresponding to photoelectric layer 35b of imaging tube 35 is scanned by electron beam 35d. FIG. 8 shows the relation between the electron beam and the spectra. The output of imaging tube 35 which is emitted every scanning line is integrated by spectrum analyzer 36.

FIG. 9(A) shows a video signal and FIG. 9(B) shows its integrated signal waveform. FIG. 9(A) shows the video signal in the (n−1)-th and n-th scanning lines shown in FIG. 8. FIG. 9(B) shows the integrated signal in each scanning line for spectrum analyzer 36. In these figures, the magnitude of the spectral response at the wavelength corresponding to the n-th scanning line is greater than that corresponding to the (n−1)-th scanning line, that is, the magnitude of the spectral response in the corresponding line is determined by integrating the corresponding spectral response sampled in accordance with the spatial relation. The integrated signal is shown in FIG. 10. It can be outputted as digital data after being converted by an A/D converter.

Operation of the cancer diagnosis device in accordance with the above-mentioned configuration will be described by referring to the operation of controller 40.

The cancer diagnosis device can operate in the first diagnosis mode in which cancer can be detected, next, in the treatment mode in which an organism affected by cancer can be sterilized by irradiation of the first laser beam pulse when a hematoporphyrin derivative has been absorbed in the organism, and in the second diagnosis mode in which healing from cancer after treatment is completed can be confirmed.

Mode selection can be performed in a cyclic way.

For the diagnosis and treatment modes of operation, FIG. 4 shows the timing diagram for light pulse emission from the first and second laser beam pulse sources and white light pulse source, and that for picking up of images. These pulse sources are synchronously operated by controller 40 so as to emit light pulses synchronized with the vertical drive at 60 Hz in the television monitoring system.

In the first and second diagnosis modes, visible light from second laser beam pulse source 23 is emitted at a wavelength of approximately 405 nm with a pulse width of approximately 30 ns during vertical blanking in the television monitoring system, synchronizing with said vertical drive.

Fluorescence occurs in a hematoporphyrin derivative selectively absorbed in the focuses of cancer when the focuses of cancer is irradiated by the laser beam. Images from the focuses of cancer are analyzed by spectroscope so that one can perform a diagnosis while minimizing the diffused light and fluorescence of an organism not affected by cancer.

An image of the focuses of cancer, obtained when the focuses are lighted by white light, is used to make a qualitative decision upon visual perception.

The white light pulse is emitted at a time between the optical pulses issued from the second laser beam source 23, and this timing relation is shown in (A) and (C) of FIG. 4.

In the figure the mark (D) shows fluorescence occurring in the focuses of cancer when these are stimulated by second laser beam pulse source 23 in (A) of the figure.

The mark (E) shows the timing when the gating pulse generator 33 opens the gate for image intensifier 32 used as an imaging device. The spectral response of fluorescence occurring in the focuses of cancer as in (D) of FIG. 4 can only be intensified because the gate opens during this period of time. The intensified spectral response is sequentially picked up each time the SIT imaging tube 35 is scanned, integrated each time the scanning line is advanced, and then displayed on display device 37.

A precise diagnosis can be done by using a graph of the spectral response, and a qualitative decision can be made by using television picture monitor 28.

A treatment of the focuses of cancer is carried out by irradiation of the laser beam pulse from said first laser beam pulse source 24.

Advantages of the cancer diagnosis device in accordance with the present invention over the conventional devices are expected to be as follows:

The spectral response of fluorescence obtained by the imaging device synchronizes with the light pulses issued from the second laser beam pulse source under control of the controller, and fluorescence stimulated by the light pulse can efficiently be picked up.

The spectral response of fluorescence occurring in the focuses of cancer, which can be obtained by the spectroscope, is picked up by the imaging device, and analyzed by the spectrum analyzer. These processes permit the inspector to perform a precise diagnosis.

Said spectral response spreading over the entire wavelength range of visible light can be picked up by horizontally scanning the imaging tube, and the output of the imaging tube is integrated by the spectrum analyzer each time the imaging tube is scanned. Energy distribution on the imaging tube in the vertical direction can effectively be analyzed by horizontal scanning.

Resolution of energy distribution on the imaging tube can be determined by the scanning line density. The third light pulse source, television camera chain, and said spectrum analyzer can be used to pick up monochrome images of the focuses of cancer and to display them online. This facilitates determination of the location where cancer exists.

The light pulse from the white light pulse source and the second laser beam pulse from the second laser beam pulse source are alternately selected by the controller so as to analyze the spectral response. Thus, spectrum analysis can successfully be accomplished.

What is claimed is:

1. Apparatus for diagnosing and treating cancer wherein a photosensitive material having an affinity to the focuses of cancer has been absorbed by said cancer, comprising an endoscope including a light pipe for transmitting light to said focuses of cancer and an image guide for observation of said focuses;

a first laser beam pulse source having a wavelength suitable for treatment of said focuses of cancer;

a second laser beam pulse source having a wavelength suitable for diagnosis of said focuses of cancer;

selector means for selectively coupling light from either said first or said second laser beam pulse source to the light pipe of said endoscope, light from the selected laser beam source impinging on said focuses of cancer;

a third white light pulse source having a wavelength suitable for observation of said focuses of cancer;

a light splitter optically coupled to said endoscope for receiving images of said focuses of cancer from the image guide of said endoscope and transmitting said image in two directions;

a spectroscope coupled to said light splitter, said spectroscope receiving light transmitted in one direction by said light splitter and generating a spectral response corresponding to two spaced fluorescent peaks emitted by said focuses of cancer when light from said second laser beam pulse source impinges on said focuses of cancer;

an imaging device coupled to the output of said spectroscope for detecting said spectral response;

spectrum analyzer means coupled to the output of said imaging means for processing the output thereof;

a display device coupled to the output of said spectrum analyzer means for graphically displaying the output of said spectrum analyzer means;

a television monitoring device coupled to said light splitter, said television monitoring device receiving light transmitted in the other direction by said light splitter; and a controller coupled to said second laser beam pulse source and to said third white light pulse source, said controller controlling the emission of light from said second and third pulse sources so that said third white light pulse source emits light during diagnosis only in the interval between the emission of pulses from said second laser beam pulse source, and controlling said imaging device so that said imaging device operates synchronously with the emission of light by said second laser beam pulse source.

2. Apparatus for diagnosing and treating cancer in accordance with claim 1, wherein said photosensitive material having an affinity to said focuses is a hematoporphyrin derivative.

3. Apparatus for diagnosing and treating cancer in accordance with claim 2, wherein said second laser beam pulse source is a color laser emitting at approximately 405 nm when stimulated by a pulse laser.

4. Apparatus for diagnosing and treating cancer in accordance with claim 3, wherein said pulse laser is an excimer laser.

5. Apparatus for diagnosing and treating cancer in accordance with claim 4, wherein said selector comprises a shutter for transmitting light from either said first laser beam source or said second laser beam source, said first and second laser beam sources responding to stimulation by said excimer laser.

6. Apparatus for diagnosing and treating cancer in accordance with claim 1, wherein said imaging device scans in the horizontal direction so as to pick up the spectral energy distribution spreading in the vertical direction.

7. Apparatus for diagnosing and treating cancer in accordance with claim 6, wherein said spectrum analyzer means integrates the output of said imaging means and wherein said display device displays the magnitude of the integrated spectral response each time the scanning is performed.

* * * * *